US007008922B2

(12) United States Patent
Goulmy et al.

(10) Patent No.: US 7,008,922 B2
(45) Date of Patent: Mar. 7, 2006

(54) H-Y ANTIGEN

(75) Inventors: Els A. J. M. Goulmy, Oegstgeest (NL); Donald F. Hunt, Charlottesville, VA (US); Victor H. Engelhard, Charlottesville, VA (US)

(73) Assignee: Rijksuniversiteit te Leiden, Leiden (NL)

( * ) Notice: Subject to any disclaimer, the term of this patent is extended or adjusted under 35 U.S.C. 154(b) by 185 days.

(21) Appl. No.: 10/328,927

(22) Filed: Dec. 24, 2002

(65) Prior Publication Data

US 2003/0181370 A1   Sep. 25, 2003

Related U.S. Application Data

(63) Continuation of application No. 09/000,217, filed as application No. PCT/NL96/00307 on Jul. 29, 1996, now Pat. No. 6,521,598.

(30) Foreign Application Priority Data

Jul. 27, 1995   (NL) .................................. 95202067

(51) Int. Cl.
       A61K 38/00    (2006.01)
(52) U.S. Cl. .......................... 514/2; 530/327; 530/328; 424/185.1
(58) Field of Classification Search ............... 514/2, 514/8; 424/184.1, 185.1; 530/237, 327, 530/328
See application file for complete search history.

(56) References Cited

OTHER PUBLICATIONS

Rufer, et al., "HA-1 and the SMCY-derived peptide FIDSY-ICQV (H-Y) are immunodominant minor histocompatibility antigens after bone marrow transplantation," (1998) Transplantation, 66:910-916.*
den Haan et al., "conservation of minor histocompatibility antigens between human and non-human primates," (1996) Eur J Immunol., 26:2680-2685.*
Agulnik et al., "Mouse H-Y encoding Smcy gene and its X chromosomal homolog Smcx," (1999) Mammalian Genome, 10:926-929.*
Janeway et al., Immunobiology, 3rd edition, Garland Publishing Inc., 1997, pp. 4:6-4:8 and G:15.*
Rammensee et al., "MHC ligands and peptide motifs:first listing," (1995) immunogenetics, 41:178-227.*

Sireci et al, "Induction and Tolerization of anti-male CD8+ cytotoxic T lymphocytes by in vivo immunization with an H-Y-derived peptide" (1999) Human Immunology, 60:764-773.*
Chai et al., "Transplantation toleranceinduced by intranasal administartion of HY peptides" (2004) Blood, 103:3951-3959.*
James et al. "Multiparity induces priming to male-specific minor histocompatibility antigen, HY, in mice and humans" (2003) Blood, 102:388-393.*
Agulnik AI, Mitcehll MJ, Lerner, JL, Woods DR, Bishop CE, "A Mouse Y Chromosome Gene Encoded by a Region Essential for Spermatogenesis and Expression of Male-Specific Minor Histocompatibility Antigens," *Human Molecular Gentics* 3(6):873-878 (1994).
den Haan JMM, Sherman NE, Blockland E, Huczko E, Koning F, Drijfhout JW, Skipper J, Shabanowitz J, Hunt DF, Engelhard VH, Goulmy E, "Identification of a Graft Versus Host Disease-Associated Human Minor Histocompatibility Antigen," *Science* 268:1476-1480 (1995).
Scott DM, Ehrmann IE, Ellis PS, Bishop CE, Agulnik AI, Simpson, E, Mitcehll MJ, "Identification of a Mouse Male-Specific Transplantation Antigen, H-Y," *Nature* 375:695-698 (1995).
Wang W, Meadows LR, den Haan JMM, Sherman NE, Chen Y, Blokland E, Shabanowitz J, Agulink AI, Hendrickson RC, Bishop CE, Hunt DF, Goulmy E, Engelhard VH, "Human H-Y: A Male-Specific Histocompatibility Antigen Dervied from the SMCY Protein," *Science* 269:1588-1590 (1955).
Campbell, Ailsa M., "Monoclonal Antibody Technology," Ed. Campbell, *Elsevier Science Publishers*, Amsterdam, NL 1-32(1985).
Yukifumi Nagai, Salvatrice Ciccarese, and Susumu Ohno, "The Identification of Human H-Y Antigen and Testicular Transformation Induced by its Interaction with the Receptor Site of Bovine Fetal Ovarian Cells," *Differentiation* 13:155-164 (1979).

* cited by examiner

*Primary Examiner*—Patrick J. Nolan
*Assistant Examiner*—Michael Szperka
(74) *Attorney, Agent, or Firm*—Hoffman & Baron, LLP

(57) ABSTRACT

The present invention relates to a peptide which is immunologically recognizable as a T cell epitope of the minor Histocompatibility antigen H-Y. The peptide comprises amino acid sequence SPSVDKARAEL (SEQ ID NO: 1) or FIDSYICQV (SEQ ID NO: 2). The peptide is obtainable from the minor Histocompatibility antigen H-Y. Providing a toxic moiety to the peptide eliminates T cells having specific binding affinity for the peptide. The peptide induces tolerance for transplantations when administered to H-Y-negative recipients.

3 Claims, 7 Drawing Sheets

H-Y ANTIGEN

This application is a continuation of U.S. application Ser. No. 09/000,217, filed on Jun. 26, 1998, issued as U.S. Pat. No. 6,521,598; which is a national stage application under 35 U.S.C. §371 of PCT/NL96/00307 filed Jul. 29, 1996. The entire disclosure of the aforementioned patent is incorporated herein by reference.

The invention relates to the field of the immunology, in, particular to the field of cellular immunology.

It is also concerned with the area of organ transplantation, grafting of tissues or cells, especially bone marrow and possible immunological reactions caused by transplantation and/or grafting and bloodtransfusion.

Since the invention concerns a sex-related proteinaceous material, encoded in nature by a sex-related gene, the invention also relates to the areas of sex linked congenital aberrations, of embryonic selection techniques, in vitro fertilization techniques, vaccination and in ovo vaccination.

Bone marrow transplantation (BMT), one of the areas the invention is concerned with and the area from which the present invention originates, finds its application in the treatment of for instance severe aplastic anaemia, leukaemia and immune deficiency diseases.

In the early days of this technique many transplants failed through rejection of the graft by the host. Transplants that did succeed, however often led to an immune response by lymphocytes present in the graft against various tissues of the host (Graft versus Host Disease (GvHD)). It is now known that the GvHD response is mainly due to the presence of major H antigens which present a transplantation barrier. Therefor it is now routine practice to graft only HLA-matched materials (either from siblings or unrelated individuals) resulting in a much improved rate of success in bone marrow transplantation. However, despite this improvement, as well as improvements in pretransplantation chemotherapy or radiotherapy and the availability of potent immunosuppressive drugs, about 20–70% of the treated patients still suffer from GvHD (the percentage is age and bone marrow donor dependent). To avoid GvHD it has been suggested to remove the cells (mature T cells) causing said reaction from the graft. This however often leads to graft failure or to recurrence of the original disease. The cells responsible for GvHD are also the cells which often react against the original aberrant cells in leukaemia (Graft versus Leukaemia response)

.Since BMT is nowadays only carried out with HLA matched grafts, the GvHD which still occurs must be caused by another group of antigens. It is very likely that the group of so called minor H antigens (mHag), which are non-MHC encoded histocompatibility antigens (unlike the major H antigens) are at least partially responsible for the remaining incidence of GvHD.

mHag's have originally been discovered in congeneic strains of mice in tumor rejection and skin rejection studies. In mice, the use of-inbred strains has shown that mHag are encoded by almost 50 different allelically polymorphic loci scattered throughout the genome (24). In humans, mHag have been shown to exist, although their overall number and complexity remains uncertain. One of the better known, though unidentified minor histocompatibility antigens is the H-Y antigen. In the first report of H-Y as a transplantation antigen Eichwald and Silmser observed that within two inbred strains of mice, most of the male-to female skin grafts were rejected, whereas transplants made in other sex combinations nearly always succeeded (1). The term H-Y antigen was introduced by Billingham and Silvers (2) because the male specific antigen can function as a classical transplantation antigen responsible for homograft rejection.

Alloimmunity to human H-Y was first demonstrated in a female patient with aplastic anaemia who was given bone marrow from her HLA-identical brother. After a period of transient chimaerism the graft was rejected. At this time after grafting her lymphocytes showed unambiguously strong MHC restricted cytotoxic T cell (CTL) responses specific for male HLA-A2 positive target cells (3,4). The clinical case not only evidenced that H-Y can function, as a transplantation barrier in man as well, but also that the recognition of the human male specific minor Histocompatibility antigen (mHag) was MHC restricted (4). The clinical relevance of H-Y as alloantigen is demonstrated especially in bone marrow transplantation (BMT) where sex-mismatch is one risk factors associated with rejection (3,4,5) or Graft-versus-Host-Disease (6,7). Sensitization to the H-Y antigen extends to organ transplantation (8–11), bloodtransfusion (12) and pregnancy (13), wherein MHC restricted T cell responses to the mHag H-Y in association with different MHC molecules are observed. To understand the impact of mHag H-Y on the outcome of organ- and bone marrow grafting we earlier studied its tissue distribution. CTL mediated lysis of tissue-derived cell and cultured cell lines of several human tissues demonstrated an ubiquitous expression (11,14,16).

In search for the biological function of the gene encoding the mHag H-Y, our earlier studies analyzing lymphocytes from sex chromosomal abnormalities with our HLA restricted H-Y specific CTL clones revealed that absence of the mHag H-Y correlated with the XO and XX karyotype (17). Subsequent studies combining DNA, and functional expression with our CTL clones analyzing lymphocytes from individuals with Y chromosomal deletions, assigned the H-Y gene encoding the mHag H-Y to a portion of interval 6 (18), to a region covering the proximal segment of the Yq euchromatin, on the long arm of the Y chromosome (19).

Besides the role of H-Y as transplantation antigen, the human Y gene controlling the expression of the mHag H-Y is possibly also functioning as a gene controlling spermatogenesis. Agulnik et al. (20) recently identified a new murine Y chromosome gene, designated Smcy, controlling spermatogenesis as well the expression of the murine male specific mHag H-Y. The Smyc gene appears to be conserved on the Y chromosome in mouse, man and even in marsupials (20). It is notable that recent studies from our laboratories show recognition of the human HA-2 and H-Y peptides on non human primates cells, transfected with human class I genes, by our human HA-2 and H-Y specific class I restricted CTL clones (21).

Until recently, little was known about the molecular nature of the mHag gene products. Recent revealing that the non-sexlinked human mHag HA-2 represents a short peptide originating from a member of the non-filament-forming class I myosin family (22). However, no information exists on the amino-acid sequence nor on the protein of the, male specific mHag H-Y.

Aiming at the identification of the human H-Y peptide, we used the HLA-B7 restricted CTL clone "5W4" (12). Clone 5W4 originates from a female aplastic anemia patient who had received mutiple transfusions (12,23).

Besides the HLA-B7 H-Y specific CTL clone, we earlier characterized HLA-A2 as well as HLA-A1 H-Y specific CTL clones (23).

We used a CD8 positive HLA-A2.1 restricted H-Y specific CTL clone, designated "1R35" (23). Besides, we also previously characterized a CD4 positive HLA-A2.1 restricted H-Y specific cytotoxic as well as proliferative T cell clone, designated as "R416" (41).

We aimed at identification of the human H-Y peptide recognized by the HLA-A2.1 restricted H-Y specific T cell clones IR35 and R416. The, same methodology as applied for the identification of the HLA-B7 restricted H-Y peptide was used.

The invention thus provides a (poly)peptide comprising a T-cell epitope obtainable from the minor Histocompatibility antigen H-Y comprising the sequence SPSVDKARAEL (SEQ ID NO:1) or FIDSYICQV (SEQ ID NO:2) or a derivative of either of these having similar immunological properties.

The two sequences specified are encoded by the SMCY gene. The first sequence is the one found using the HLA-B7 restricted H-Y specific T-cell clone, The second is the one found using the HLA-A2.1 restricted clones.

The way these sequences are obtained is described herein. An important part of this novel method of arriving at said sequences is the purification and the choice of the starting material. Said novel method is therefor also part of the scope of this invention. However, now that the sequence is known, it is of course no longer necessary to follow that method, because the peptides can easily be made synthetically, as is well known in the art. Since routine techniques are available for producing synthetic peptides, it is also within the skill of the art to arrive at analogs or derivatives of the explicitly described peptides, which analogs and/or derivatives may have the same or at least similar properties and or activity. On the other hand analogs which counteract the activity of the explicitly described peptides are also within the skill of the art, given the teaching of the present invention. Therefor derivatives and/or analogs, be it of the same or different length, be it agonist or antagonist, be it peptide like or peptidomimetic, are part of the scope of this invention.

A preferred embodiment of the present invention are the peptides with the sequences SPSVDKARAEL (SEQ ID NO:1) and/or FIDSYICQV (SEQ ID NO:2). This does not imply that other peptides are not suitable. This will for a large part depend on the application and on other properties of the peptides, which were not all testable within the scope of the present invention.

The peptides and other molecules according to the invention find their utility in that they may be used to induce tolerance of the donor immune system in H-Y negative donors, so that residual peripheral blood lymphocytes in the eventually transplanted organ or the bone marrow, as it may be do not respond to host H-Y material in an H-Y positive recipient. In this way GvHD may be prevented. On the other hand tolerance may be induced in H-Y negative recipients in basically the same way, so that upon receipt of an organ or bone marrow from an H-Y positive donor no rejection on the basis of the H-Y material occurs.

For tolerance induction very small doses can be given repeatedly, for instance intravenously, but other routes of administration may very well be suitable too. Another possibility is the repeated oral administration of high doses of the peptides. The peptides may be given alone, or in combination with other peptides, or as part of larger molecules, or coupled to carrier materials in any suitable excipients.

Further applications of the peptide derivatives thereof lie in the prophylactic administration of such to transplanted individuals to prevent GvHD. This can be done with either agonists, possibly in combination with an adjuvant, or with antagonists which may block the responsible cells. This can be done with or without the concomittant administration of cytokines.

Furthermore the peptides or antibodies thereto can be used in so called "magic bullet" applications, whereby the peptide or the antibody is coupled to a toxic substance to eliminate certain subsets of cells.

Diagnostic applications are clearly within the skill of the art. They include, but are not limited to H-Y typing, detection of genetic aberrancies and the like.

Other therapeutical applications of the peptide include the induction of tolerance to H-Y proteins in H-Y related (auto)immune diseases, such as possibly in Rheumatoid arthritis. On the other hand they may be used in vaccines in H-Y related (auto)immune diseases.

For the sake of illustration a number of applications is cited below.

The H-Y peptide or its derivatives can be used to prevent harmful reaction of the recipient towards the donor or vice versa; in all forms of transplantation i.e. organs, tissues and bone marrow. Assuming that residual donor peripheral blood lymphocytes (PBL)'s in the transplanted organ could react with and/or against host PBL's and even could cause GvHD, the H-Y peptide could be used to induce tolerance in living organ (kidney, liver, gut, skin) of H-Y negative donors for H-Y positive patients. In bone marrow transplantation, the H-Y peptide (given alone or in combination with other peptides) can be used to induce tolerance in the living bone marrow donor. The peptide(s) can be given orally, intravenous or otherwise.

In all forms of organ (including cornea), tissue (including heartvalves and skin) and bone marrow transplantation with living or cadaveric donors, the H-Y peptide could be used to induce tolerance in H-Y negative recipients of organ and tissue transplants from H-Y positive donors. In case of bone marrow transplantation, tolerance must be induced in female donors for male recipients. The tolerance induction can be achieved by clinical application of the H-Y peptide systematically, i.v., locally, orally, as eye-drops.

The H-Y peptides could act in a non-allelic restricted manner (thus promiscuous) implicating that its applicability to inducing tolerance is not restricted to the HLA type of the female donors and female recipients and donors The H-Y peptides or their derivatives can be applied to generate reagents and/or medicine. They can be used as Graft-versus-Host disease and rejection prophylaxis administration to the transplanted individual either with or without adjuvant of a) a H-Y peptide
b) H-Y peptide analogues, including left or right turning peptides
c) H-Y peptide antagonists Usage of the H-Y sequence information to generate, for immunomodulatory purposes:

a) anti-idiotypic T cells
b) anti-idiotypic B cells
c) human monoclonal antibodies The H-Y peptides or their derivatives can be used as a marker for sex linked congenital or other diseases.

They can be used for the generation of a genetic probe enabling screening for the congenital sex-linked disorders.

The genetic probe can be used for genetic counseling, population genetics and pre-natal diagnostic.

The defect can be repaired by genetic engineering.

The peptides and other molecules according to the invention can also be used for the production of anti-conceptive drugs.

Furthermore the peptides and other molecules according to the invention can be used for the production of cytotoxic T lymphoctes (CTL) with specificity for the H-Y sequence.

The H-Y specific CTL can be used for selection of male embryos in X linked recessive disorders.

The invented molecules can be applied to generate reagents and/or medicine for
a) determination of foetal erythrocytes in maternal circulation.
b) intra uterine diagnostics
c) use prior to implantation for in vitro fertilization.
d) determination of chimerism.

Veterinary applications include:
a) embryonic selection.
b) in vitro fertilization.
c) vaccination and in ovo vaccination
d) anti-conception.

On the basis of the peptides described herein genetic probes can be produced which can be used to screen for the gene encoding the protein. On the other hand such probes may be useful in detection kits as well. On the basis of the peptides described herein anti-idiotypic B cells and/ or T cells and antibodies can be produced. All these embodiments have been made possible by the present disclosure and therefor are part of the present invention.

The techniques to produce these embodiments are all within the skill of the art.

Dose ranges of peptides and antibodies and/or other molecules according to the invention to be used in the therapeutical applications as described herein before are usually designed on the basis of rising dose studies in the clinic. The doses for peptides may lie between about 0.1 and 1000 µg per kg bodyweight, preferably between 1 and 10 µg per kg bodyweight.

Reconstitution of the H-Y epitope with HPLC fractionated peptides extracted from HLA-B7 molecules. (A) HLA-B7 molecules were immunoaffinity purified from 2×10$^{10}$ H-Y positive JY cells. Peptides were eluted from B7 molecules with 10% acetic acid, pH 2.2, filtered through a 10 kD cut-off filter and fractionated on a C18 reverse phase column. Buffer A was 0.1% heptafluorobutyric acid (HFBA); buffer B was 0.1% HFBA in acetonitrile. The gradient consisted of 100% buffer A (0–20 mm), 0 to 12% buffer B (20 to 25 mm), and 12 to 50% buffer B (25 to 80 mm) at a flow rate of 200 µl/min. 60 fractions of 200 µl each were collected from 20 to 80 mm. (B) Fractions 28 and 29 from the separation shown in (A) were rechromatographed with the same acetonitrile gradient, but using trifluoroacetic acid (TFA) instead of HFBA as the organic modifier. For both panels, 3% of each peptide fractions were preincubated with 1,000 $^{51}$Cr-labeled T2-B7 cells at room temperature for 2 hours. CTLS were then added at an effector to target ratio of 10 to 1, and further incubated at 37° C. for 4 hours. Background lysis of T2-B7 by the CTL in the absence of any peptides was ~3% in (A) and ~4% in (B); positive control lysis of JY was 75% in (A) and 74% in (B).

FIG. 2.

Figure 1A:
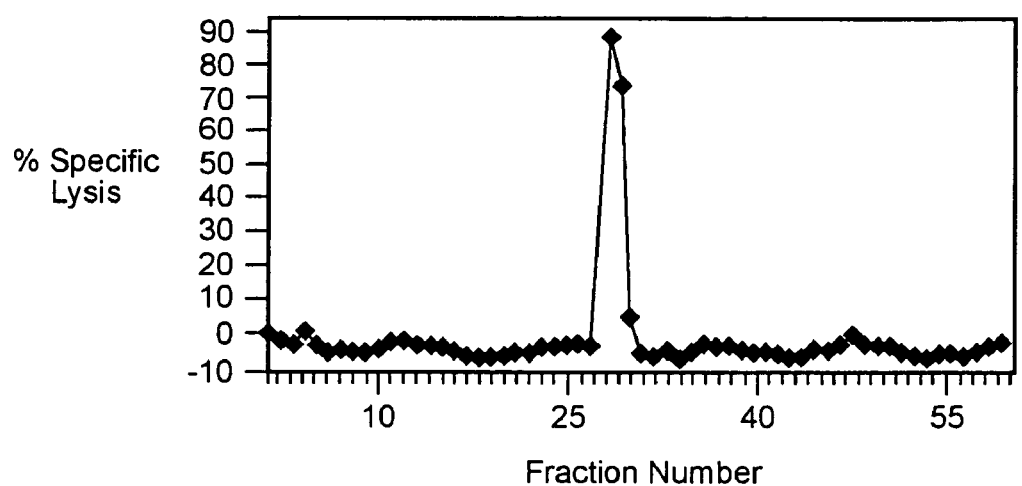
FIG. 1

Determination of candidate H-Y peptide by mass spectrometry combined with $^{51}$Cr release assay. HPLC fraction 14 from the separation shown in FIG. 1B was chromatographed with an on-line microcapillary column effluent splitter as previously described (11,13). One-fifth of the effluent was deposited into µl of culture media in microtiter plate wells for analysis with CTLs as in FIG. 1. The remaining four-fifths of the material were directed into the electrospray ionization source, and mass spectra of the peptides deposited in each well were recorded on a triple-quadruple mass spectrometer (Finnigan-MAT, San Jose, Calif.). (♦), H-Y epitope reconstitution activity measured as percent specific lysis; (■), abundance of peptide 1171 measured as ion current at m/z 391.

FIG. 3.

Figure 1B:
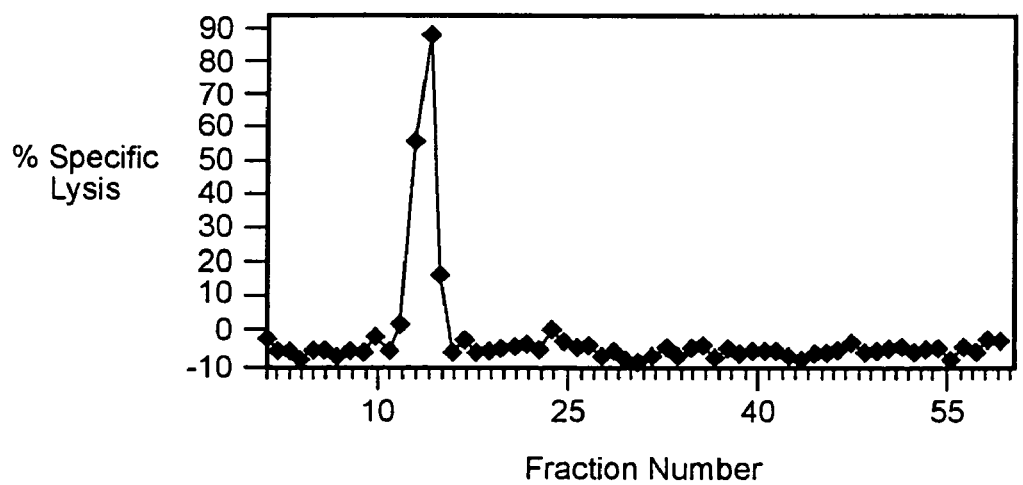

CAD mass spectrum of peptide 1171 after conversion the R residue to ornithine. material from second dimension HPLC fraction 14 shown in FIG. 1B was treated with 70% hydrazine hydrate for 1 hour. The CAD mass spectrum was recorded on the (M+2H)+2 ion at m/z 566.

FIG. 4.

H-Y epitope reconstitution with synthetic peptides. Synthetic peptides were purified to homogeneity by reverse phase-HPLC on a Vydac C4 column. Purity was established on an analytical RP column and the quantity of each peptide was confirmed by comparing the area of the peak with that of a standard peptide. The identity of the peptides was confirmed by mass spectrometry. $^{51}$Cr release was assayed at an effector to target ratio of 10 to 1 on T2-B7 cells that had been incubated with the indicated concentration of SMCY peptide SPSVDKARAEL (SEQ ID NO:1) (♦), or SMCX peptide SPAVDKAQAEL (SEQ ID NO:3) (■).

FIG. 5.

Binding of synthetic peptides to purified HLA-B7. HPLC-purified test peptides were assayed for the ability to inhibit the binding of the iodinated endogenous B7 peptide APRTYVLLL (SEQ ID NO:4) to purified HLA-B7 as previously described (40). (♦), SMCY peptide SPSVDKARAEL (SEQ ID NO:1); (■) SMCX peptide SPAVDKAQAEL (SEQ ID NO:3); (Δ), APRTLVLLL (SEQ ID NO:5), an endogenous peptide bound to HLA-B7; (x) LLDVPTAAV (SEQ ID NO.6), an endogenous peptide bound to HLA-A2.1 as the negative control.

FIG. 6.

HLA-A2 molecules were immunoaffinity purified from 10$^{10}$ DM cells. Peptides were eluted according to the methodology as described in legend to FIG. 1.

DESCRIPTION OF THE INVENTION

As with other mHag, the recognition of H-Y by T lymphocytes is MHC-restricted (3,24,25), and it has been shown that some H-Y antigens are peptides derived from cellular proteins that are presented on the cell surface in association with MHC class I molecules (26). We have developed a technique for the identification of individual peptides that are bound to MHC molecules and recognized as antigens by T cells. By combining microcapillary liquid chromatography/electrospray ionization mass spectrometry with T cell epitope reconstitution assays, we previously identified peptide antigens recognized by T cells specific for human melanoma (27), human xenografts (28), and a non-sex-linked human mHag (22). We now report the identification of a peptide antigen recognized by a human cytotoxic T lymphocyte (CTL) clone that is H-Y specific and restricted by the class I MHC molecule HLA-B7, as well as a peptide antigen that is recognized by two HLA-A2.1 restricted CTL clones., To isolate endogenously processed H-Y peptides, HLA-B7 molecules were purified by affinity chromatography from the H-Y positive, B lymphoblastoid cell line, JY (29). The associated peptides were extracted in acid and separated from high molecular weight material by ultrafiltration as previously described (31), and subsequently fractionated by reverse-phase high-performance liquid chromatography (HPLC) (27). Aliquots of each fraction were incubated with HLA-B7 positive, H-Y negative T2-B7 target cells in order to assay for the ability to reconstitute the epitope recognized by an HLA-B7-restricted, H-Y specific CTL clone, 5W4 (ref. 12). A single peak of reconstituting activity was observed (FIG. 1A, fraction 28 and 29), which was rechromatographed using a different organic modifier. Although a single active peak of reconstituting activity was also observed from this separation (FIG. 1B, fraction 14, 15 and 16), it still contained more than 100 distinct peptide species, as assessed by electrospray ionization tandem mass spectrometry.

Figure 2:
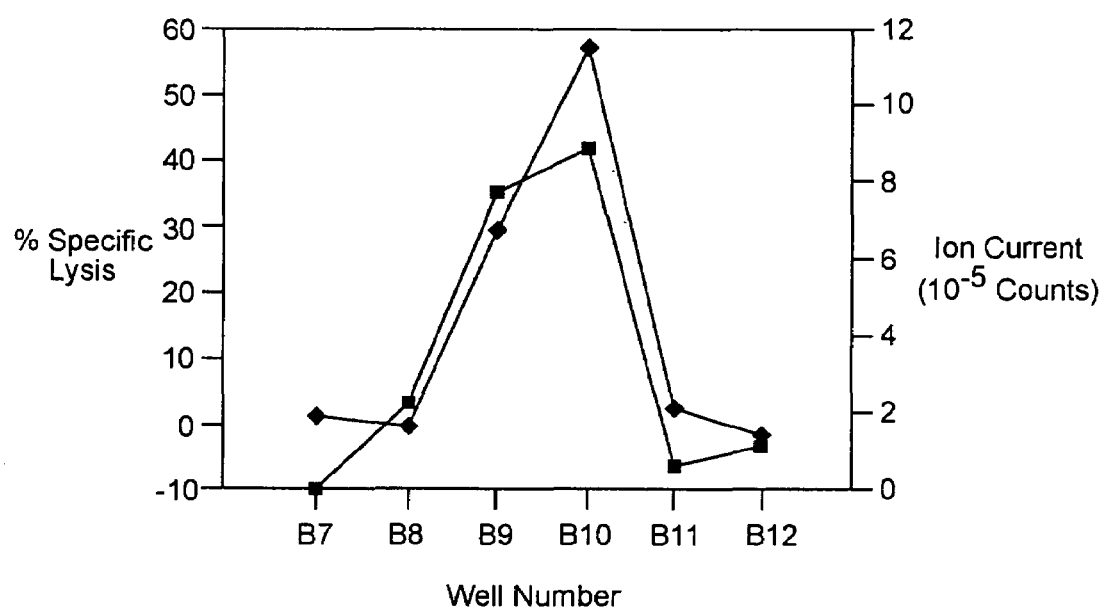

To identify active H-Y peptides in this mixture, we, applied each active fraction separately to a microcapillary HPLC column and split the effluent following the separation (11): Four-fifths of the effluent was directed into the mass spectrometer for analysis, while one-fifth was simultaneously directed into a 96-well microtiter plate for a subsequent epitope reconstitution assay. The amount of the H-Y sensitizing activity in each well was correlated to signals observed in the mass spectrum, and therefore to the abundance of different peptide species. By comparing the profile of H-Y activity and the ion abundance data (FIG. 2), we were able to identify an (M+3H)+3 ion at a mass-to-charge ratio (m/z) of 391 (neutral molecular mass=1171), whose abundance correlated with the amount of H-Y epitope reconstituting activity. Further confirmation of the importance of peptide 1171 was provided by the demonstration that a peptide with an identical mass and collision-activated dissociation (CAD) spectrum was also present in HLA-B7 associated peptides extracted from a second H-Y positive B lymphoblastoid line, DM, but absent from a spontaneous H-Y antigen loss variant of this cell, DM(–) (33).

Figure 3A:
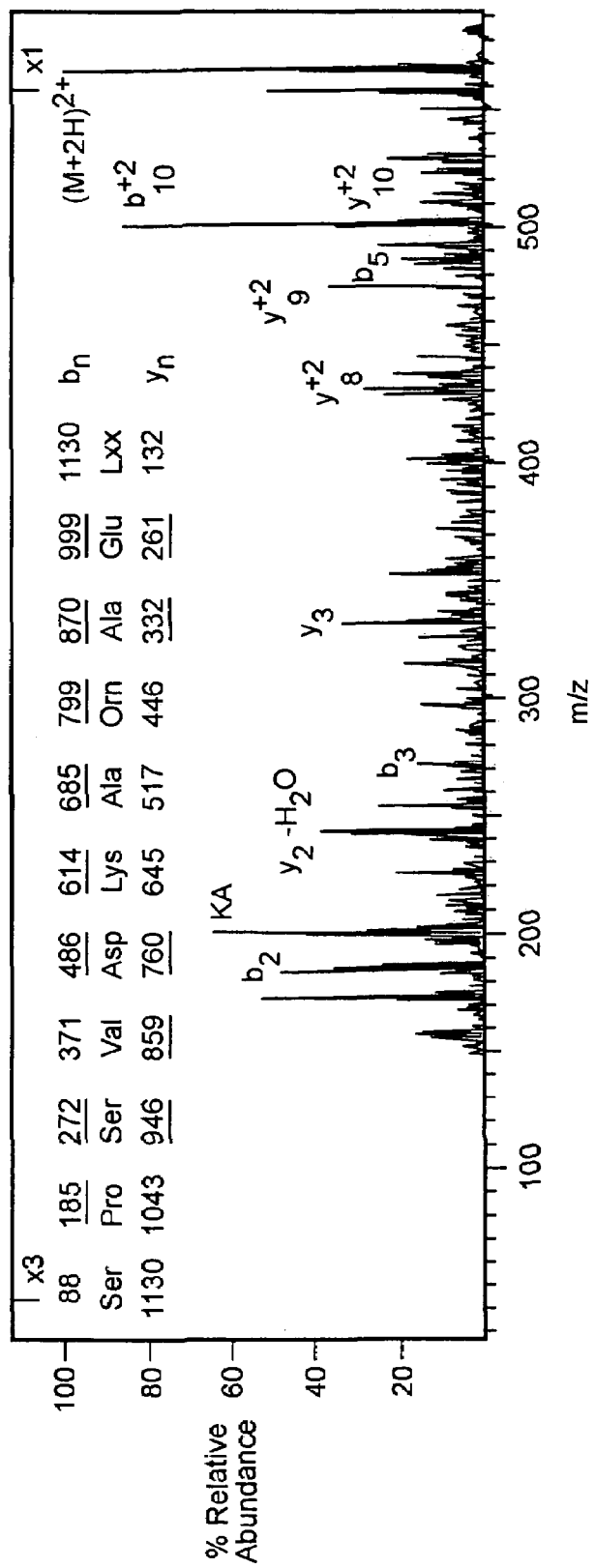
Figure 3B:
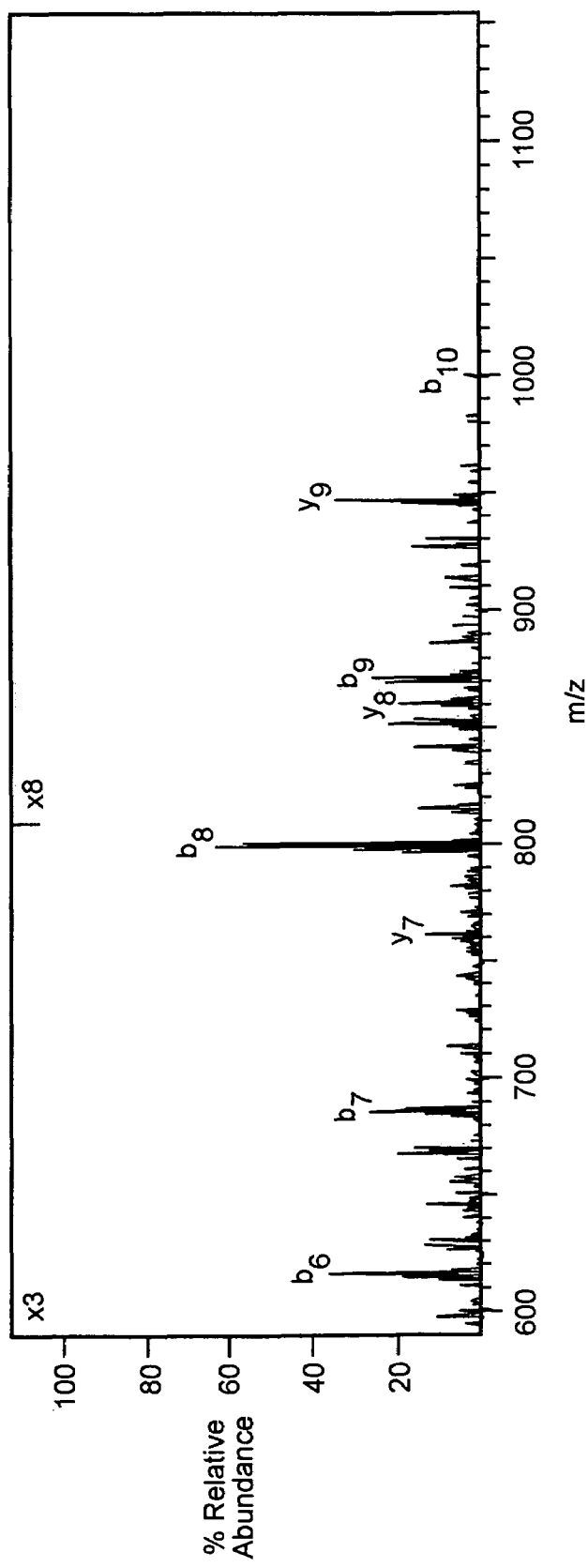

Assignment of a complete amino acid sequence to the 1171 peptide from the CAD mass spectrum recorded at the 20 fmol level proved difficult due to the absence of high mass fragment ions containing the amine terminus (b-type ions). A series of single and/or doubly charged fragment ions containing the amine terminus (b-type ions). A series of single and/or doubly charged fragment ions containing the carboxyl terminus (y-type ions) identified the C-terminal residue as either L or I and the first six amino acids as SPSVDK (SEQ ID NO:7). The difference in molecular mass between this partial sequence and that of the full length peptide suggested the presence of four additional residues, for a total length of 11. Since the candidate peptide existed exclusively in the gas phase as an (M+3H)+3 ion, and underwent mass shifts of 42 and 84 Da on conversion to the corresponding methyl ester and acetylated derivative, respectively, two of the remaining residues were assigned as R and either D or E. Only two combinations of four residues (AREA (SEQ ID NO: 8) and GRDV (SEQ ID NO:9)) meet the above criteria and satisfy the missing mass of 427 Da. CAD spectra recorded on synthetic peptides suggested that R could not be located at either position 7 or 10. Data bases were searched for proteins containing peptides with these characteristics, and a sequence consistent at 9 out of 11 positions was found in residues 909–919 of the protein encoded by a gene called XE169 or SMCX (34), which is located on the X chromosome. A homolog of SMCX, called SMCY, is located on the Y chromosome (20). This protein (35) contains a sequence (residues 902–912) that is consistent at 11 out of 11 positions, and has the expected mass of 1171 Da. A CAD mass spectrum recorded on the naturally processed material after conversion of the R residue to ornithine confirmed that its sequence was identical to that found in SMCY protein (FIG. 3).

Figure 6:
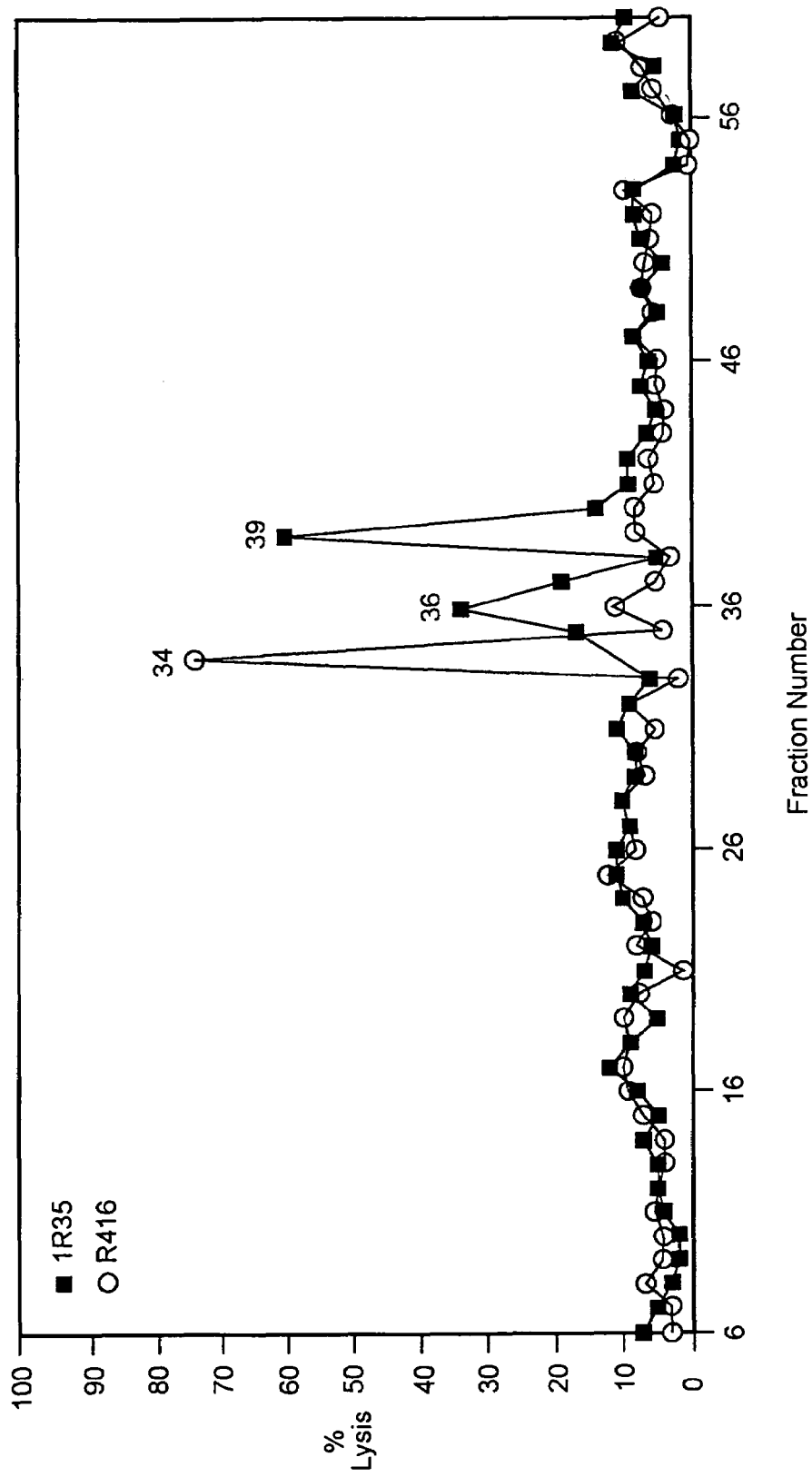

In the same manner as described above for the HLA-B7 restricted T-cell clone, the peptide recognized by two HLA-A2.1 T-cell clones was identified. In short the HLA-A2.1 restricted H-Y specific T cell clone R416 recognizes HPLC fraction 34, the HLA-A2.1 restricted H-Y specific T clone 1R35 recognizes HPLC fractions 36 and 39 (FIG. 6). The amino acid sequence analyses and H-Y reconstitution assays demonstrate that both HLA-A2.1 restricted H-Y specific T cell clones recognize peptide sequence FIDSYICQV (SEQ ID NO:2) with a m/z ratio of 544 or the cystinylated form of the same peptide with a m/z ratio of 604.

Figure 4:
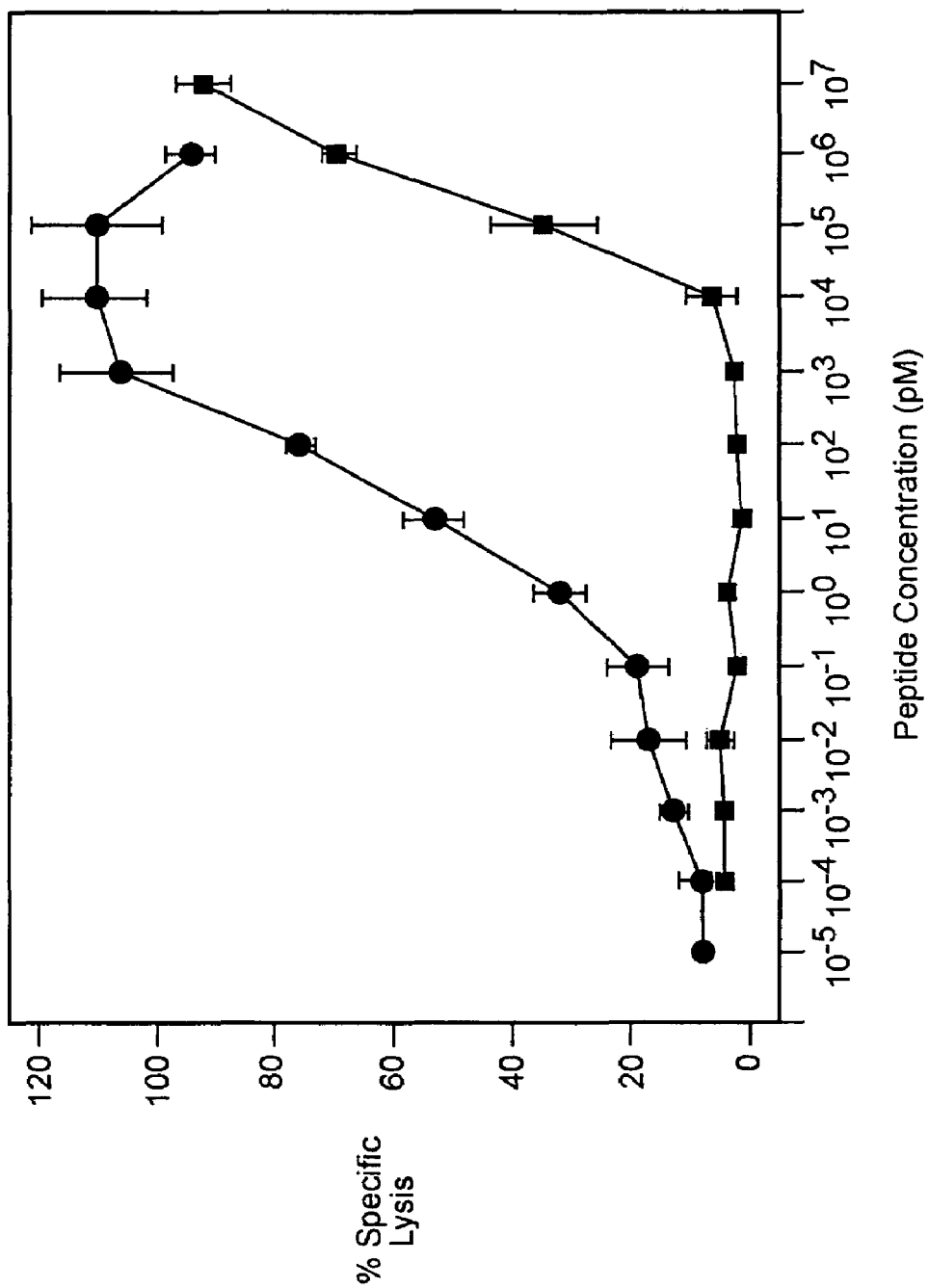
Figure 5:
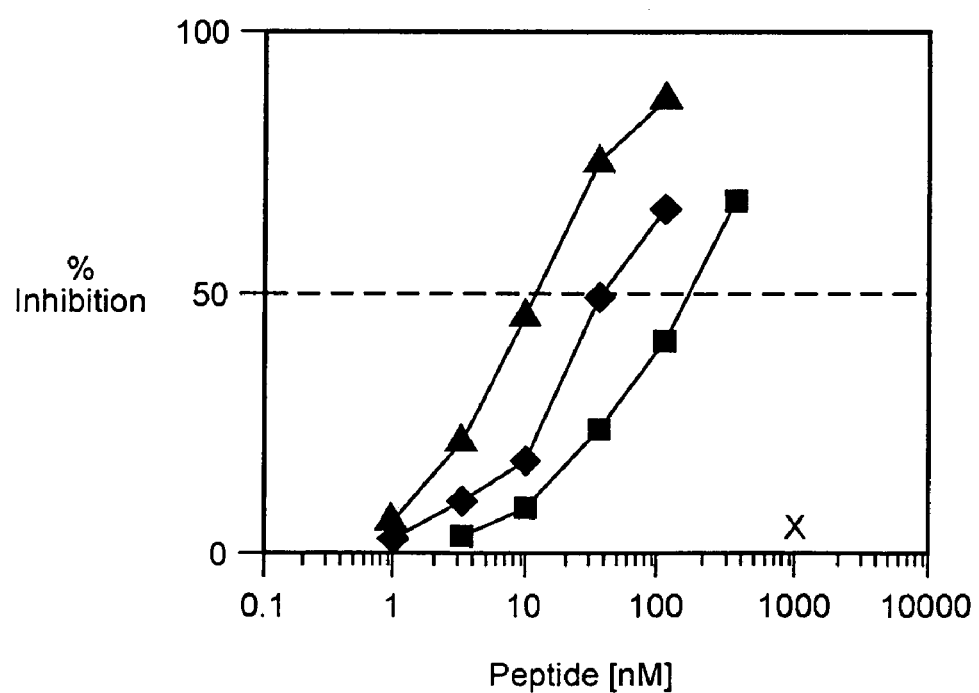

A synthetic peptide corresponding to the 11 residue SMCY sequence (SPSVDKARAEL (SEQ ID NO:1)) was found to sensitize T2-B7 cells for recognition by the H-Y specific CTL clone. Half-maximal lysis was achieved at a peptide concentration of 10 pM (FIG. 4). The corresponding peptide derived from the sequence of the X chromosomal homolog, SMCX, has substitutions of A for S at position 3 and Q for R at position 8. Although this peptide also was able to sensitize T2-B7 cells for recognition, comparable levels of killing were only achieved by using a 10,000-fold higher peptide concentration. Binding studies showed that the concentration of the SMCY peptide that inhibited the binding of an iodinated standard peptide to purified HLA-B7 by 50% (IC50) was 34 nM, while the IC50 for the SMCX peptide was 140 nM (FIG. 5). Thus, the significant difference in the ability of the SMCY and SMCX peptides to sensitize targets for T cell recognition is almost entirely due to the fine specificity of the T cell receptor, rather than to differences in MHC binding affinities. The SMCX peptide is also present in naturally processed peptide extracts of HLA-B7, although its abundance is only 25% of that of the SMCY peptide (33). Based on all of this information, it is concluded that the peptide epitopes representing the HLA-B7 restricted H-Y antigen is derived from the protein encoded by SMCY, which is also true for the HLA-A2.1 recognized peptide, also encoded by SMCY.

The location of the SMCY gene and the control of its expression fit well with those expected of the H-Y antigen based on previous work. Deletion mapping in humans has placed the HY locus to a portion of interval 6 on the long arm of the human Y chromosome (18), and SMCY maps to this same interval (20). H-Y antigens are expressed ubiquitously in different tissues (5,15), and expression of SMCY has been detected in all male tissues tested (20). One interesting issue is whether the H-Y epitope peptides presented by other MHC molecules will also be derived from SMCY SMCY and SMCX are 85% identical at the amino acid sequence level, and the SMCX gene is expressed ubiquitously from both the active and the inactive X chromosomes in both mice and human (34,36). Therefore, self-tolerance to SMCX will limit the number of SMCY peptides that could give rise to H-Y epitopes in association with different MHC molecules. On the other hand, SMCY contains almost 1500 residues, and the over 200 amino acid sequence differences between it and SMCX are scattered relatively uniformly throughout its length. Thus, there is the potential to generate a large number of distinct SMCY-specific peptides as H-Y epitopes. It is still an open question whether the H-Y epitope peptides presented by other MHC molecules are also derived from SMCY. Genetic mapping of the mouse Y chromosome has suggested at least two and up to five distinct loci encoding H-Y antigens (37). Interestingly, a murine epitope restricted by HL-2Kk has also been shown to be derived from the murine Smcy protein (38). The demonstration that two H-Y epitopes from either mouse or human are derived from the same protein makes SMCY the prime target in searching other H-Y epitopes.

The identification of the protein that gives rise to an H-Y antigen culminates 40 years of uncertainty regarding its origin. However, the function of SMCY, as well as the homologous SMCX, remains unclear. Both proteins share significant sequence homology to retinoblastoma binding protein 2, which has been suggested to be a transcription factor (39). Nonetheless, this and other H-Y specific peptides are candidates for immunomodulatory approaches in bone marrow transplantation. They may also form the basis for genetic probes to be used for prenatal diagnosis in sex-linked congenital abnormalities, as well as for investigating minimal residual disease and chimerism.

REFERENCES

1. E. J. Eichwald, C. R. Silmser.: Transplant Bull; 148–149, 1955.
2. R. E. Billingham, W. K. Silvers: Studies on tolerance of the Y chromosome antigen in mice. J. Immunol. 85: 14–26, 1960.
3. E. Goulmy, A. Termijtelen, B. A. Bradley, J. J. van Rood. Alloimmunity to human H-Y. Lancet ii: 1206, 1976.
4. E. Goulmy, A. Termijtelen, B. A. Bradley, J. J. van Rood. Y-antigen killing by T cells of women is restricted by HLA. Nature 266: 544–545, 1977.
5. P. J. Voogt, W. E. Fibbe, W. A. F. Marijt, E. Goulmy, W. F. J. Veenhof, M. Hamilton, A. Brand, F. E. Zwaan, R. Willemze, J. J. van Rood, J. H. F. Falkenburg. Rejection of bone marrow graft by recipient derived cytotoxic T lymphocytes against minor histocompatibility antigens. Lancet 335: 131–134, 1990.
6. M. M. Bortin for the Advisory Committee of the International Bone Marrow Transplant Registry: Acute graft-versus-host disease following bone marrow transplantation in humans: prognostic factors. Transplant Proc 19: 2655–2657, 1987.
7. Report from the International Bone Marrow Transplant Registry: Bone Marrow Transplant 4: 221–228, 1989.
8. E. Goulmy, B. A. Bradley, Q. Lansbegen J. J. van Rood. The imporance of H-Y incompatibility in human organ transplantation. Transplantation 25: 315–319, 1979.
9. P. F. Pfeffer, E. Thorsby. HLA-restricted cytotoxicity against male specific (H-Y antigenafter acute rejection of an HLA identical sibling kidney. clonal distribution of the cytotoxic cells. Transplantation 33: 52–56, 1982.
10. Y. Beck, M. Sekimata, S. Nakayama et al. Expression of human minor Histocompatibility antigen on cultured kidney cells. Eur. J. Immunol. 23: 467–472, 1993.
11. E. Goulmy, J. Pool, E. van Lochem and (H. Völker-Dieben. The role of human minor Histocompatibility antigens in graft failure: a mini-review. Eye 9: 180–184, 1995.
12. E. Goulmy, J. D. Hamilton and B. A. Bradley Anti-self HLA may be clonally expressed. J. Exp. Med. 149: 545–550, 1979.
13. D. P. Singal, Y. J. Wadia, N. Naipaul. In vitro cell-mediated cytotoxicity to the male specific (H-Y) antigen in man. Human Immunol. 2: 45–53, 1981.
14. P. J. Voogt, E. Goulmy, W. E. Fibbe, W. F. J. Veenhof, A. Brand, J. H. F. Falkenburg. Minor histocompatibility antigen H-Y is expressed on human haematopoietic progenitor cells. J. Clin. Invest. 82: 906–912, 1988.
15. M. de Bueger, A. Bakker, J. J. van Rood, F. van der Woude and E. Goulmy. Tissue distribution of human minor histocompatibility antigens. Ubiquitous versus restricted tissue distribution indicates heterogeneity among human cytotoxic T lymphocyte-defined non-MHC antigens. J. of Immunol. 149, 5: 1788–1794, 1992.
16. D. van der Harst, E. Goulmy, J. H. F. Falkenburg, Y. M. C. Kooij-Winkelaar, S. A. P. van Luxemburg, H. M. Goselink and A. Brand. Recognition of minor Histocompatibility antigens on lymphocytic and myeloid leukemic cells by cytotoxic T-cell clones. Blood 83: 1060–1066, 1994.
17. E. Goulmy, A. van Leeuwen, E. Blokland, E. S. Sachs and J. P. M. Geraedts. The recognition of abnormal sex chromosome constitution by HLA-restricted anti-H-Y cytotoxic T cells and antibody. Immunogenetics 17: 523–531, 1983.
18. M. A. Cantrell, J. S. Bogan, E. Simpson, J. N. Bicknell, E. Goulmy, P. Chandler, R. A. Pagon, D.C. Walker, H. C. Thuline, J. M. Graham Jr., A. de La Chaeplle, D. C. Page and C. M. Disteche. Deletion mapping of H-Y antigen to the long arm of the human Y chromosome. Genomics 13: 1255–1260, 1992.
19. A. J. O'Reilly, N. A. Affara, E. Simpson, P. Chandler, E. Goulmy and M. A. Ferguson-Smith. A molecular deletion map of the Y chromosome long arm defining x and autosomal homologous regions and the localisation of the HYA locus to the proximal region of the Yq euchromatin Human Mol. Gen. 1: 379–385, 1992.
20. A. Agulnik, M. J. Mitchell, J. L. Lerner, D. R. Woods and C. Bishop. A mouse Y chromosome gene encoded by a region essential for spermatogenesis and expression of male specific minor Histocompatibility antigens. Human Molecular Genetics 3: 873–878, 1994.
21. J. M. M. den Haan, J. Pool, N. Sherman, E. Blokland, R. Bontrop, V. H. Engelhard, D. F. Hunt and E. Goulmy. Minor Histocompatibility antigens are conserved between human and non-human primates. Manuscript submitted for publication.
22. J. M. M. den Haan, N. E. Sherman, E. Blokland, E. Huczko, F. Koning, J-W. Drijfhout, J. Skipper, J. Shabanowitz, D. F. Hunt, V. H. Engelhard, E. Goulmy. Identification of graft versus host disease-associated human minor Histocompatibility antigen. Science 268: 1476–1480, 1995.
23. E. Goulmy. In: Transplantation Reviews vol. 2. {.J. Morris and N. C. Tilney Eds. Saunders, Philadelphia, 1988: pp 29–53.
24. B. Loveland, E. Simpson, Immunol. Today 7, 223 (1986).
25. R. D. Gordon, E. Simpson, L. E. Samelson, J. Exp. Med. 142, 1108 (1975).
26. O. Rotzschke, K. Falk, H. J. Wallny, S. Faath, H. G. Rammensee, Science 249, 283 (1990).
27. A. L. Cox et al, Science 264, 716 (1994).
28. R. A. Henderson et al, Proc. Natl. Acad. Sci. USA 90, 10275 (1993).
29. M. J. Turner et al, J. Biol. Chem. 250, 4512 (1975);
30. P. Parham, B. N. Alpert, H. T. Orr, J. L. Strominger, J. Biol. Chem. 252, 7555 (1977).
31. D. F. Hunt et al, Science 255, 1261 (1992);
32. E. L. Huczko et al, J. Immunol. 151, 2572 (1993).
33. L. R. Meadows, W. Wang, N. E. Sherman, J. M. den Haan, unpublished results.
34. J. Wu et al, Human Molecular Genetics 3, 153 (1994);
35. A. I. Agulnik, C. E. Bishop; unpublished results.
36. J. Wu et al, Nature Genetics 7, 491 (1994).
37. T. R. King et al, Genomics 24, 159 (1994)
38. D. M. Scott et al, unpublished results.
39. A. R. Fattaey et al, Oncogene 8, 3149 (1993).
40. J. Ruppert et al, Cell 74, 929 (1993); Y. Chen et al, J. Immunol. 152, 2874 (1994); A. Sette et al, J. Immunol. 153, 5586 (1994).
41. M. de Bueger, A. Bakker, E. Goulmy, Existence of mature human CD4$^+$ T cells with genuine class I restriction, Eur. J. Immunol. 1992, 22: 875–878.

What is claimed is:

1. A method for inducing tolerance for transplants in a human that expresses HLA-B7 or a human that expresses HLA-A2.1, comprising administering to the human that expresses HLA-B7, and that is in need of tolerance for transplants, a tolerance-inducing amount of a peptide consisting of amino acid sequence SPSVDKARAEL (SEQ ID NO:1), or comprising administering to the human that expresses HLA-A2.1, and that is in need of tolerance for transplants, a tolerance-inducing amount of a peptide consisting of amino acid sequence FIDSYICQV (SEQ ID NO:2), whereby rejection of transplants or graft-versus-host reaction is reduced.

2. A method according to claim 1, comprising administering the peptide to an H-Y-negative donor prior to transplantation in an amount sufficient to inhibit graft-versus-host reaction by a graft in an H-Y-positive graft recipient following transplantation.

3. A method according to claim 1, comprising administering the peptide to an H-Y-negative recipient prior to transplantation in an amount sufficient to inhibit rejection of an H-Y-positive graft in the recipient following transplantation.

* * * * *

SEQUENCE LISTING

<160> NUMBER OF SEQ ID NOS: 9

<210> SEQ ID NO 1
<211> LENGTH: 11
<212> TYPE: PRT
<213> ORGANISM: Homo sapiens

<400> SEQUENCE: 1

Ser Pro Ser Val Asp Lys Ala Arg Ala Glu Leu
 1               5                  10

<210> SEQ ID NO 2
<211> LENGTH: 9
<212> TYPE: PRT
<213> ORGANISM: Homo sapiens

<400> SEQUENCE: 2

Phe Ile Asp Ser Tyr Ile Cys Gln Val
 1               5

<210> SEQ ID NO 3
<211> LENGTH: 11
<212> TYPE: PRT
<213> ORGANISM: Homo sapiens

<400> SEQUENCE: 3

Ser Pro Ala Val Asp Lys Ala Gln Ala Glu Leu
 1               5                  10

<210> SEQ ID NO 4
<211> LENGTH: 9
<212> TYPE: PRT
<213> ORGANISM: Homo sapiens

<400> SEQUENCE: 4

Ala Pro Arg Thr Tyr Val Leu Leu Leu
 1               5

<210> SEQ ID NO 5
<211> LENGTH: 9
<212> TYPE: PRT
<213> ORGANISM: Homo sapiens

<400> SEQUENCE: 5

Ala Pro Arg Thr Leu Val Leu Leu Leu
 1               5

<210> SEQ ID NO 6
<211> LENGTH: 9
<212> TYPE: PRT
<213> ORGANISM: Homo sapiens

<400> SEQUENCE: 6

Leu Leu Asp Val Pro Thr Ala Ala Val
 1               5

<210> SEQ ID NO 7
<211> LENGTH: 6
<212> TYPE: PRT
<213> ORGANISM: Homo sapiens

<400> SEQUENCE: 7

Ser Pro Ser Val Asp Lys

-continued

```
1               5

<210> SEQ ID NO 8
<211> LENGTH: 4
<212> TYPE: PRT
<213> ORGANISM: Homo sapiens

<400> SEQUENCE: 8

Ala Arg Glu Ala
  1

<210> SEQ ID NO 9
<211> LENGTH: 4
<212> TYPE: PRT
<213> ORGANISM: Homo sapiens

<400> SEQUENCE: 9

Gly Arg Asp Val
  1
```